US00PP28478P3

(12) United States Plant Patent
Klemm et al.

(10) Patent No.: US PP28,478 P3
(45) Date of Patent: Oct. 3, 2017

(54) POINSETTIA PLANT NAMED 'NPCW15237'

(50) Latin Name: *Euphorbia pulcherrima*
Varietal Denomination: NPCW15237

(71) Applicant: Klemm+Sohn GmbH & Co. KG, Stuttgart (DE)

(72) Inventors: Nils Klemm, Stuttgart (DE); Guido Von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 114 days.

(21) Appl. No.: 14/757,277

(22) Filed: Dec. 11, 2015

(65) Prior Publication Data

US 2017/0172041 P1 Jun. 15, 2017

(51) Int. Cl.
*A01H 5/02* (2006.01)

(52) U.S. Cl.
USPC ..... Plt./307

(58) Field of Classification Search
USPC ..... Plt./263.1, 302, 303, 307
See application file for complete search history.

*Primary Examiner* — Susan McCormick Ewoldt
*Assistant Examiner* — Karen Redden
(74) *Attorney, Agent, or Firm* — Barbara Campbell; James M. Weatherly; Cochran Freund & Young, LLC

(57) ABSTRACT

A new poinsettia plant particularly distinguished by having bright red bracts, a triangular plant form, an upright growth habit, and good keeping quality, is disclosed.

1 Drawing Sheet

Genus and species: *Euphorbia pulcherrima.*
Variety denomination: 'NPCW15237'.

BACKGROUND OF THE NEW PLANT

The present invention comprises a new and distinct variety of poinsettia, botanically known as *Euphorbia pulcherrima* and hereinafter referred to by the variety name 'NPCW15237'. 'NPCW15237' was derived as a selection from the 2009 self-pollination in Nairobi, Kenya of the poinsettia 'NPCW10164' (U.S. Plant Pat. No. 22,597) which is commercially known as 'Christmas Day', having red bracts.

In October 2010, a single bright red plant was selected in Stuttgart, Germany from lines of the self-pollination of poinsettia 'NPCW10164'. In May 2011, 'NPCW15237' was first asexually propagated by apical vegetative cuttings. 'NPCW15237' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Bright red bracts;
2. A triangular plant form;
3. An upright growth habit; and
4. Good keeping quality.

DESCRIPTION OF THE PHOTOGRAPH

This new poinsettia plant is illustrated by the accompanying photograph which shows an overall view of the plant. The photograph is of a plant approximately seventeen-weeks-old grown indoors in Stuttgart, Germany in November 2013. The colors shown are as true as can be reasonably obtained by conventional photographic procedures.

DESCRIPTION OF THE NEW VARIETY

The following detailed descriptions set forth the distinctive characteristics of 'NPCW15237'. The data which define these characteristics were collected from asexual reproductions carried out in Stuttgart, Germany. Data was collected on nineteen-week-old plants (after potting) grown indoors in Stuttgart, Germany under greenhouse conditions in November 2015. Color references are to The R.H.S. Colour Chart of The Royal Horticultural Society of London (R.H.S.), 5$^{th}$ edition (2007).

Classification:
- *Family.*—Euphorbiaceae.
- *Species.*—*Euphorbia pulcherrima.*
- *Common name.*—Poinsettia.
- *Variety.*—'NPCW15237'.

Parentage: Selection from the self-pollination of poinsettia 'NPCW10164'.

Growth:
- *Time to produce a rooted cutting.*—4 weeks.
- *Blooming habit.*—Intermittent.
- *Flowering response time.*—Approximately 52 days.
- *Keeping quality.*—Good.

Plant description:
- *Form.*—Triangular.
- *Growth habit.*—Upright (broad angle).
- *Height.*—25.0 cm to 30.0 cm.
- *Width.*—About 25.0 cm.
- *Number of branches.*—5 to 7.
- *Average number of inflorescences per plant.*—6.
- *Disease and pest resistance.*—None observed.

Propagation:
- *Type cuttings.*—Apical cuttings.
- *Time to produce a rooted cutting.*—4 weeks.

*Rooting habit and root color*.—Freely branching and root color is RHS NN 155D.

Lateral branches:

*Color*.—RHS 143A overlaid with RHS 183A.
*Length*.—16.0 cm to 18.0 cm.
*Internode length*.—1.0 cm to 3.0 cm.
*Diameter*.—0.5 cm to 1.0 cm.
*Branching habit*.—Freely branching.
*Number of lateral branches per plant*.—5 to 7.
*Texture*.—Smooth.

Leaves:

*Quantity*.—5 to 6 per lateral branch.
*Arrangement*.—Alternate.
*Number of lobes on the leaf blade*.—0 to 2.
*Depth of the deepest sinus of the leaf blade*.—0.5 cm.
*Shape*.—Ovate.
*Apex*.—Acute.
*Base*.—Obtuse.
*Margin*.—Serrate.
*Length*.—7.0 cm to 11.0 cm.
*Width*.—5.0 cm to 8.0 cm.
*Texture* (*both surfaces*).—Smooth.
*Vein color*.—Upper surface: Transparent. Lower surface: RHS 139D.
*Variegation*.—Absent.
*Venation pattern*.—Reticulate.
*Color*.—Mature foliage: Upper surface: RHS 139A. Lower surface: RHS 137B. Immature foliage: Upper surface: RHS 144B. Lower surface: RHS 143C.
*Leaf petiole*.—Length: 2.0 cm to 4.0 cm. Diameter: 0.2 cm to 0.3 cm. Color: Upper (part) surface: RHS 184A. Lower (part) surface: RHS 184A with a greenish background. Texture: Smooth. Strength: Medium.

Inflorescence:

*Lastingness of inflorescence on the plant*.—3 weeks.
*Natural flowering season*.—End of November.
*Diameter*.—19.0 cm to 25.0 cm.
*Height*.—2.0 cm to 4.0 cm.
*Fragrance*.—Absent.

Bracts:

*Number of bracts per inflorescence*.—7 to 8.
*Shape*.—Ovate.
*Apex*.—Acute.
*Base*.—Obtuse.
*Margin*.—Entire.
*Size*.—Length: 8.0 cm to 11.0 cm. Width: 5.0 cm to 8.0 cm.
*Texture* (*both upper and lower surfaces*).—Smooth.
*Venation pattern*.—Reticulate.
*Vein color*.—Upper surface: RHS 185A. Lower surface: RHS 181A.
*Bract color*.—Upper surface: Between RHS 46A and RHS 46B. Lower surface: Close to RHS 47A.
*Bract petiole*.—Length: 1.0 cm to 2.0 cm. Diameter: 0.2 cm. Color: Upper (part) surface: RHS 185B. Lower (part) surface: RHS 181A.
*Texture*.—Smooth.
*Strength*.—Medium.

Cyme:

*Diameter:* 1.5 cm.
*Cyathia number*.—4 to 6 per inflorescence.
*Deformation of glands of the cyathium*.—Absent.
*Cyathium*.—Shape: Ovoid. Diameter: 0.3 cm to 0.5 cm. Length: 0.4 cm to 0.7 cm. Color: RHS 143C.
*Peduncle*.—Color: RHS 144C. Length: 0.2 cm to 0.3 cm. Diameter: 0.2 cm. Texture: Smooth. Strength: Strong.
*Nectar cups*.—Number: 1 per cyathium. Diameter: 0.1 cm. Length: 0.2 cm to 0.3 cm. Color: RHS 13A to RHS 14C.

Reproductive organs:

*Stamen quantity*.—5 to 10 per cyanthium.
*Stamen shape*.—Ovoid.
*Filament length*.—0.2 cm.
*Filament color*.—RHS 46A.
*Pollen quantity*.—Moderate.
*Pollen color*.—RHS 9A to RHS 12A.
*Gynoecium*.—Not observed.

Fruit and seed set: None observed.

COMPARISON WITH PARENTAL LINE AND KNOWN VARIETY

'NPCW15237' is distinguished from its parent 'NPCW10164' as described in Table 1.

TABLE 1

| Characteristic | Variety 'NPCW15237' | Parent 'NPCW10164' |
|---|---|---|
| Number of bracts per inflorescence | 7 to 8 | 8 to 10 |
| Number of leaves per lateral branch | 5 to 6 | 8 to 15 |
| Vigor | Low | Medium |

'NPCW15237' can be compared to the commercial Poinsettia plant variety 'Premium Red' (Patent status unknown). Differences between the two varieties are described in Table 2.

TABLE 2

| Comparison with Similar Variety | | |
|---|---|---|
| Characteristic | Variety 'NPCW15237' | 'Premium Red' |
| Bract color | Bright red | Dark red |
| Bract size | Medium | Large |

We claim:

1. A new and distinct variety of poinsettia plant named 'NPCW15237' as illustrated and described herein.

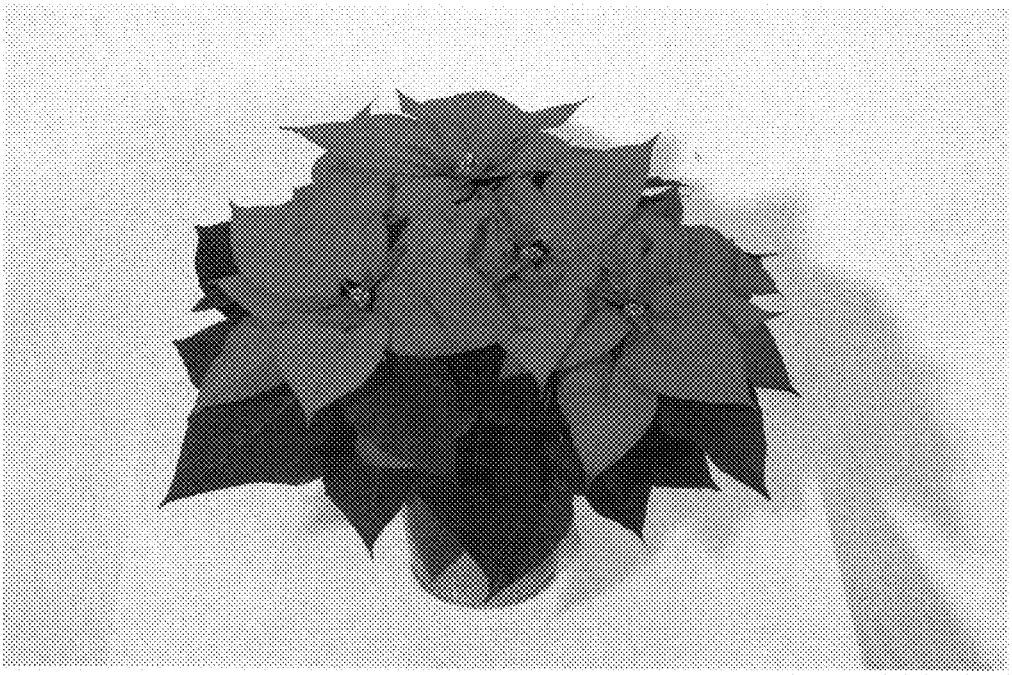

* * * * *